(12) United States Patent
Kaska (10) Patent No.: US 8,042,549 B2
(45) Date of Patent: Oct. 25, 2011

(54) STERILE RADIOLOGICAL DRAPE

(76) Inventor: Serge Kaska, Encinitas, CA (US)

( * ) Notice: Subject to any disclaimer, the term of this patent is extended or adjusted under 35 U.S.C. 154(b) by 334 days.

(21) Appl. No.: 12/248,291

(22) Filed: Oct. 9, 2008

(65) Prior Publication Data

US 2009/0255541 A1  Oct. 15, 2009

Related U.S. Application Data

(60) Provisional application No. 61/043,644, filed on Apr. 9, 2008.

(51) Int. Cl.
*A61B 19/08* (2006.01)
*H01J 35/16* (2006.01)

(52) U.S. Cl. .................. 128/852; 378/203

(58) Field of Classification Search .......... 128/846, 128/849, 852, 853, 854, 855, 856; 378/193, 378/203, 204
See application file for complete search history.

(56) References Cited

U.S. PATENT DOCUMENTS

| 7,044,132 B2 | 5/2006 | Masini |
| 2006/0020152 A1 | 1/2006 | Theobald et al. |
| 2006/0076024 A1 | 4/2006 | Duarte |
| 2006/0201521 A1 | 9/2006 | Masini |
| 2008/0006278 A1* | 1/2008 | Henke-Sarmento et al. . 128/849 |

FOREIGN PATENT DOCUMENTS

| WO | WO2006/038096 A1 | 12/1996 |
| WO | WO2007/041093 A1 | 4/2007 |

OTHER PUBLICATIONS

International Search Report for International Application No. PCT/US2009/039858, date completed May 21, 2009, date mailed Jun. 4, 2009, 2 pgs.
Written Opinion of the International Searching Authority for International Application No. PCT/US2009/039858, date completed May 21, 2009, date mailed Jun. 4, 2009, 6 pgs.

* cited by examiner

*Primary Examiner* — Patricia Bianco
*Assistant Examiner* — Tarla Patel
(74) *Attorney, Agent, or Firm* — John D. Wright; Dickinson Wrigh, PLLC (57) ABSTRACT

A collapsible sterile drape designed to encase the non-sterile portion of a radiological unit is provided. The sterile radiological drape is designed to expand to encompass the radiological unit as it rotates into and is move through the sterile field for imaging during surgery, and then to collapse to protect the sterile portion of the drape when the radiological unit is removed from the surgical field.

30 Claims, 8 Drawing Sheets

STERILE RADIOLOGICAL DRAPE

RELATED APPLICATIONS

This application claims priority to Provisional Application No. 61/043,644 filed Apr. 9, 2008, the contents of which are incorporated herein in their entirety.

FIELD OF THE INVENTION

The current invention is directed to an improved sterile radiological drape; and more particularly to a collapsible sterile radiological drape.

BACKGROUND OF THE INVENTION

Hospital-acquired infections are a growing cause of concern. These infections are estimated to affect about 2 million patients annually and cause an estimated 100,000 deaths. Moreover, beyond the loss of life resulting from these infections they also create enormous costs for the healthcare industry. For example, some studies have indicated that each patient that comes down with a central-line-associated bloodstream infection results in an average $26,839 loss to the hospital. As a result of the growing problems associated with these infections, about 16 states have passed laws covering how hospitals handle patients to decrease infection risks. Accordingly, reducing the number of infections patients contract while in hospitals would not only benefit patients but also healthcare industry as a whole.

Surgical site infection has been estimated to occur in about 15% of clean surgery and 30% of contaminated surgery. Using plastic drapes to protect the wound from organisms that may be present on the surrounding skin during surgery is one strategy used to prevent surgical site infection. However, the current draping technique uses what is called a half-sheet, which is a plain rectangular sheet that is draped over the patient and hangs down over the sides of the operating table. In standard operations such a draping method is relatively simple and effective; however, in some cases it is necessary to introduce large pieces of unsterilized equipment into the operating room. For example, in spinal and orthopedic surgery it is often necessary to take radiological images of various parts of the patient's body as the surgery proceeds. This in turn requires the positioning and repositioning of the radiological equipment around the surgical table.

Figure 1:
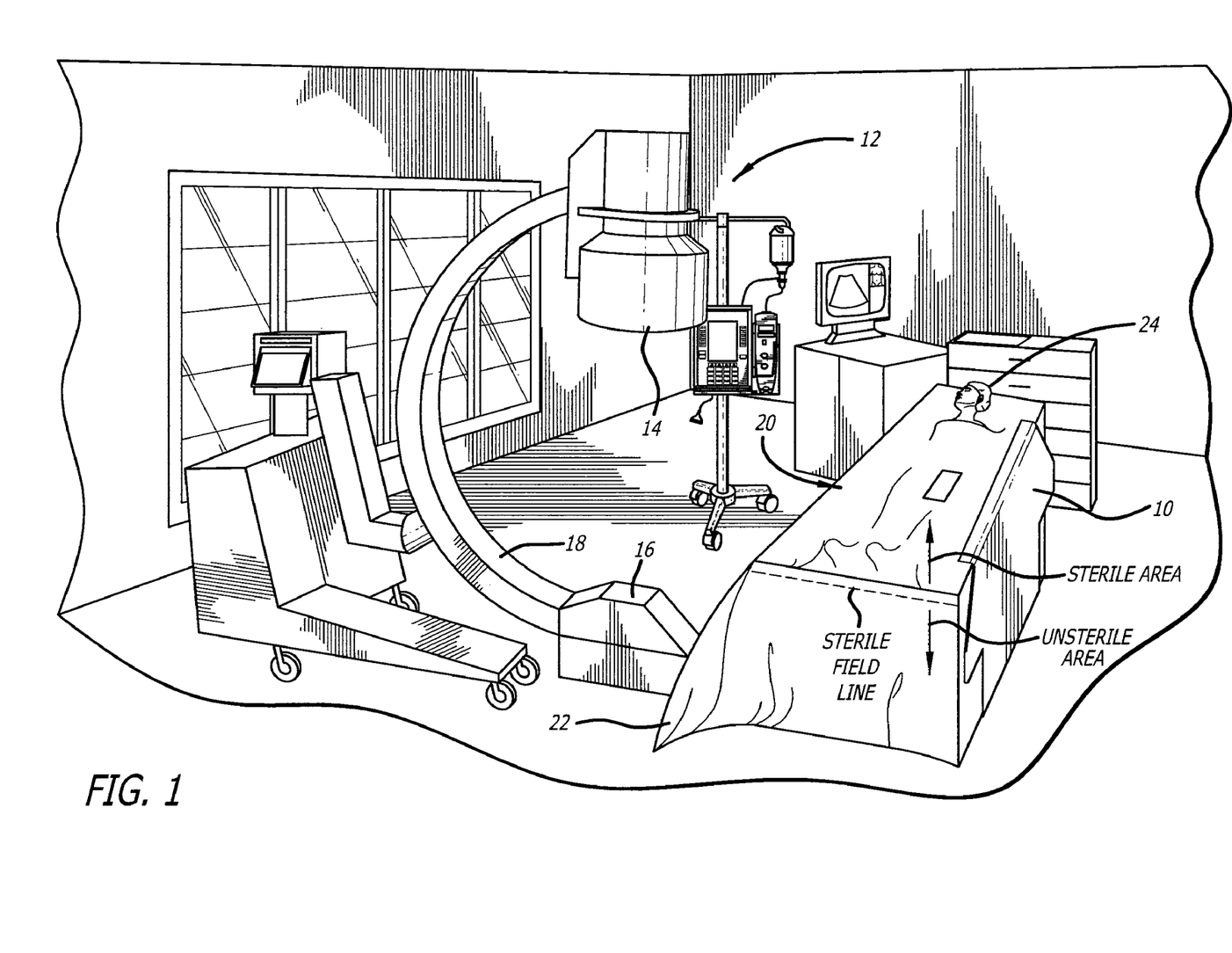
FIG. 1 provides a perspective view of an embodiment of a sterile radiological drape in accordance with the current invention attached to the surgical table prior to application on the C-arm fluoroscopy unit.
Figure 3:
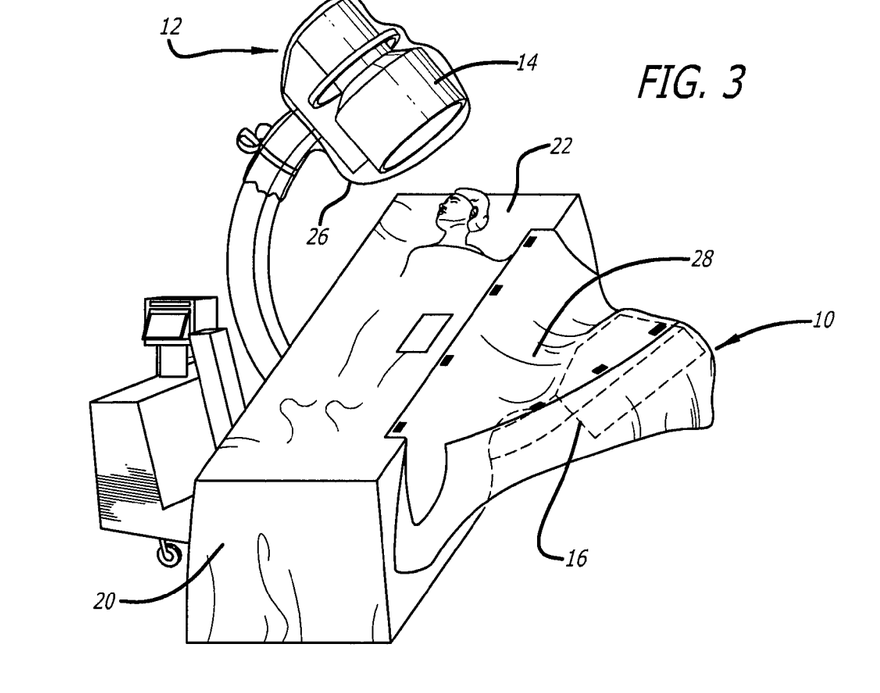
FIG. 3 provides a perspective view of an embodiment of a sterile radiological drape in use during an operation in accordance with the current invention.
Figure 4:
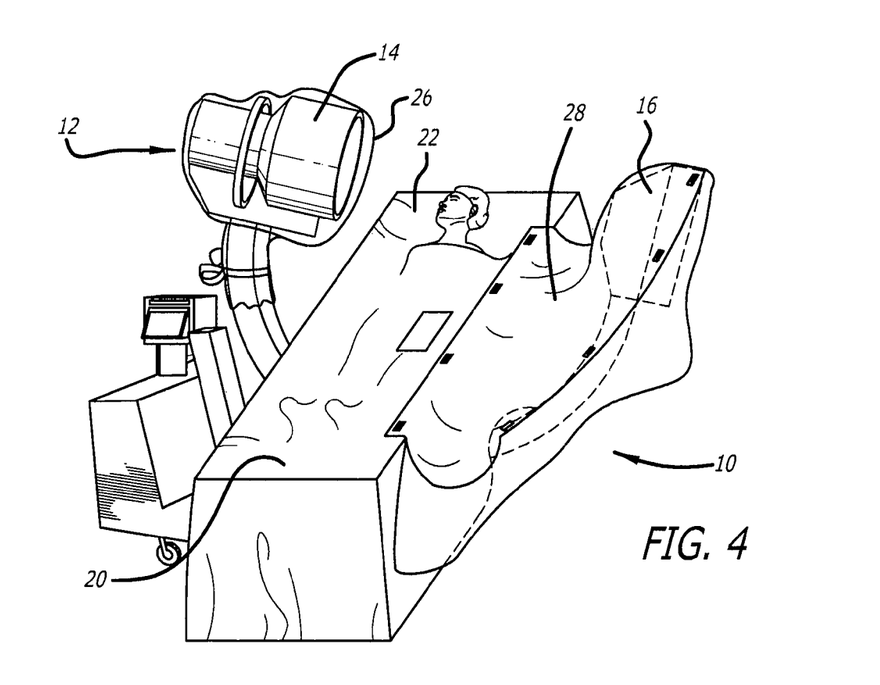
FIG. 4 provides a perspective view of an embodiment of a sterile radiological drape in operation in accordance with the current invention.

The most common piece of radiological equipment is a C-arm fluoroscopy unit. An illustration of a C-arm fluoroscopy unit is shown in FIG. 1. When an image of a patient is taken the armature of the fluoroscopy unit must be inserted beneath and through the opposite side of the surgical table. Then the arm is raised upward so that it is positioned lateral to the area of the patient to be imaged. The result, as shown in FIGS. 3 and 4, is that the two unsterilized ends of the fluoroscopy unit are directly adjacent to the surgical table. These large unsterile arms create an immediate contamination hazard to the surgeons and the entire surgical field.

Draping the armatures with conventional half-sheets, particularly as the armatures are moved to various locations during surgery, is a cumbersome process that often requires the use of multiple half-sheets. Moreover, there is not a single accepted methodology for draping these pieces of radiological equipment, leading to the use of any number of idiosyncratic and unstandardized methods. Improper draping can result in surgical delay and frequently violates sterility, exposing patients to unnecessary risk of infection. Finally, because the equipment in question is typically moved in and out of the surgical field multiple times during surgery, even if the device is properly draped initially, there is no established system for storing the drape in a sterile manner and then systematically redraping the equipment.

A few sterile drapes specifically designed for use with radiological equipment have recently been introduced; however, the currently available radiological drapes all require the use of a framework that fixes the drape into position relative to the surgical table. (See, e.g., U.S. Patent Publication Nos. 2006/0201521 and 2006/0076024, the disclosures of which are incorporated herein by reference.) Unfortunately, such immobile draping systems can obstruct substantial portions of the operating theater. Moreover, the fixed nature of these frameworks prevents the surgical team from repositioning these prior art radiological draping systems during the operation without increasing the risk that the sterile field will be contaminated. Accordingly, a need exists for an improved collapsible sterile sheet system specifically designed for use with radiological equipment.

SUMMARY OF THE INVENTION

The current invention provides a collapsible sterile drape designed to encase the non-sterile portion of a mobile radiological imaging device as it rotates into and is move through the sterile field for imaging during surgery.

In one embodiment the sterile imaging drape takes the form of a flexible enclosure where the enclosure can repeatedly take one of either an expanded or a collapsed configuration. In such an embodiment, when the enclosure is in the expanded position the enclosure is designed to be sufficiently sized to receive and cover at least a portion of the mobile imaging device, and when the enclosure is in the collapsed position the sterile portion of the enclosure is folded inwardly such that the upper it is substantially shielded from external contamination, such as from external objects or the non-sterile surfaces of the enclosure itself.

In another embodiment the sterile imaging drape also includes at least one anchor fastener designed to fixedly attach the enclosure to an object within the sterile field, such as the operating table, patient, or patient drape. In such an embodiment the fastener may be an adhesive, hooks and loop, snap, latch, hook, clamp, clip and zipper.

In still another embodiment the sterile imaging drape is integrated into a conventional patient drape in a position such that when the patient drape is positioned over the patient, at least a portion of the sterile imaging drape is positioned within the sterile field.

In yet another embodiment the sterile imaging drape also includes at least one reusable enclosure fastener designed to secure the enclosure in the collapsed configuration. In such an embodiment the fastener may be an adhesive, hooks and loop, snap, latch, hook, clamp, clip and zipper. In one exemplary embodiment the reusable enclosure fastener is formed of cooperative interconnection means disposed on opposing faces of the enclosure.

In still yet another embodiment the sterile imaging drape is asymmetric. In such an embodiment the asymmetry may come from the construction of one or both ends of the enclosure. In one exemplary embodiment the end of the enclosure positioned nearest the operating table is designed with a vertical length short enough that it does not impede the movement of the imaging equipment beneath the operating table and into the enclosure. In another exemplary embodiment, the end of the enclosure positioned away from the operating table is designed with a vertical length long enough to fully cover the imaging equipment regardless of the vertical alignment of the mobile imaging equipment relative to the operating table. In any of the above embodiments, the side portions of the enclosure may have a vertical length that matches either the portion nearest the operating table, the portion distant from the operating table, or a varying profile that tapers between the distant portion and the near portion of the enclosure.

In still yet another embodiment the sterile imaging drape is formed with at least one pleat.

In still yet another embodiment the sterile imaging drape is formed of a material selected from one of plastic, cloth, paper, synthetics and composites thereof.

In still yet another embodiment the sterile imaging drape further includes a reinforcement liner disposed along the edges of the enclosure.

In still yet another embodiment the sterile imaging drape may be partially transparent to allow for the visualization of the mobile imaging device.

In still yet another embodiment the sterile imaging drape includes an active material selected from the group of antibacterial agents, antifungal agents and antiviral agents. In such an embodiment, the active material may be applied to the drape by coating, imbuing, and impregnating.

In still yet another embodiment the sterile imaging drape includes a unique visual indicator to differentiate the sterile and non-sterile portions of the drape.

In still yet another embodiment the sterile imaging drape includes at least one weighted element incorporated into at least one of the lower edges of the enclosure to keep the drape resting against the floor.

In still yet another embodiment the sterile imaging drape includes at least one tailoring means for conforming the shape of the enclosure to the mobile imaging equipment. In such an embodiment the tailoring means can be selected from the group of fasteners, elasticized gathers and pleats.

In still yet another embodiment the sterile imaging drape is designed for use with a fluoroscopy unit having a C-arm.

In still yet another embodiment the sterile imaging drape is dimensioned to cover the length of the operating table.

The invention is also directed to a method of draping a patient using the sterile imaging drape of the instant invention. In such an embodiment the sterile imaging drape of the current invention is attached to an object within the sterile field of the operating theater, such as, for example, the operating table, the patient or the patient drape.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein.

DETAILED DESCRIPTION OF THE INVENTION

The current invention provides a collapsible sterile drape designed to encase the lower non-sterile portion of a radiological unit as it rotates into and is move through the sterile field for imaging during surgery. In general terms the sterile C-arm drape of the current invention is a disposable, collapsible drape having engineered into it a collapsible sterile pouch which accepts the lower portion of a radiological unit, such as the lower C-arm of a fluoroscopy unit, as it rotates into the sterile field for imaging during surgery, and then can be collapsed and stored in such a way as to maintain the sterility of the sterile pouch of the drape when the radiological unit is removed from the surgical field.

Figure 2:
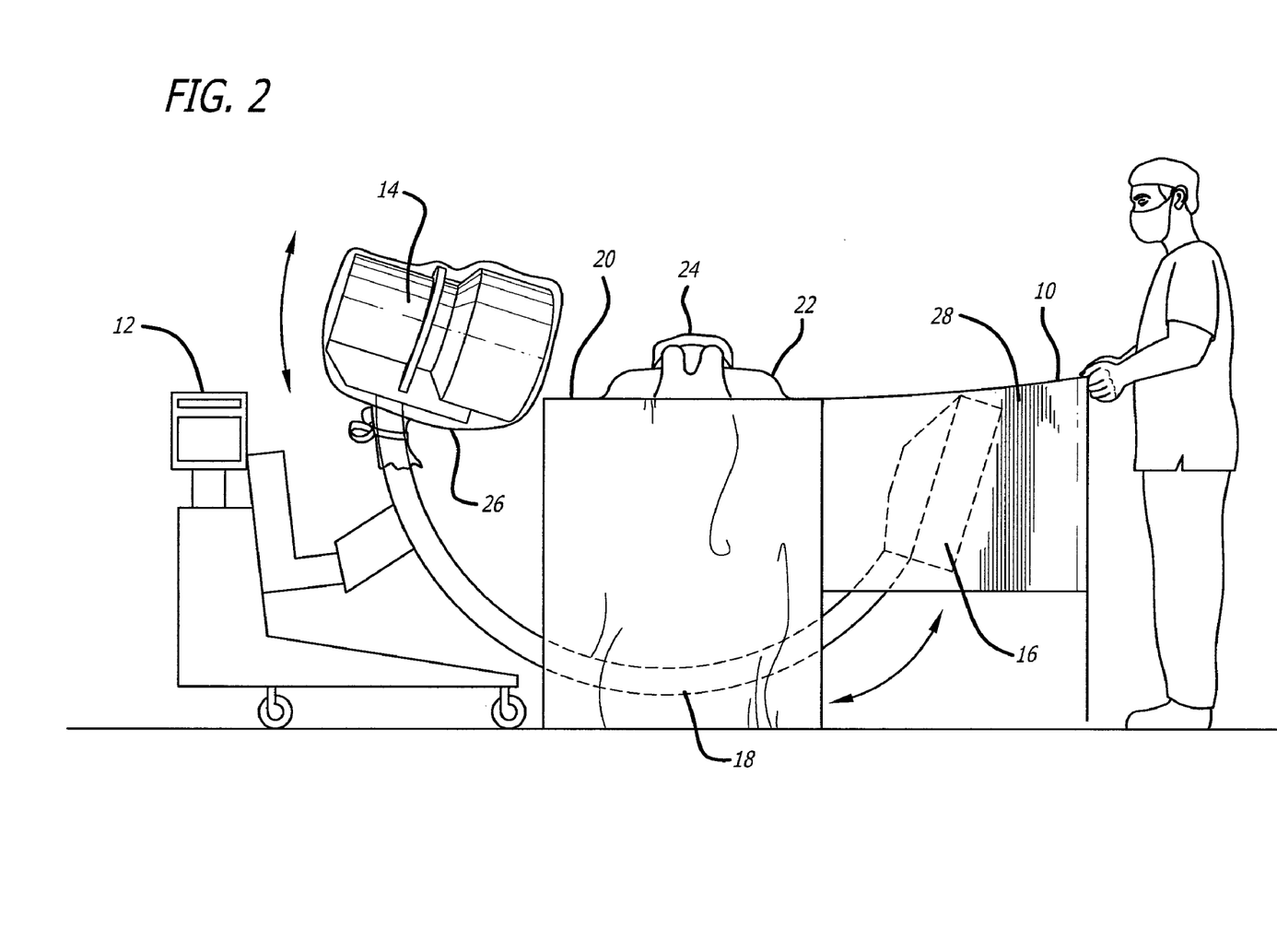
FIG. 2 provides a side view of an embodiment of a sterile radiological drape in use during an operation in accordance with the current invention.

The drape of the current invention will be better understood with reference to the figures. Referring initially to FIGS. 1 to 3, the present invention is directed to a radiological sterile drape (10) for use in surgical environments for procedures involving the use of radiological equipment in which two planes of imaging (horizontal and vertical are required), such as, for example, a C-arm fluoroscopy unit (12). Prior to describing the sterile radiological drape of the current invention, a fuller description of the equipment it will be used with will be provided.

First, the radiological unit (12) shown in the figures is one of the most common used designs and comprises upper (14) and lower (16) imaging units interconnected by a "C" shaped arm (18). During operation, as shown in FIG. 2, the lower imaging unit (16) and the "C" shaped arm (18) pass beneath the surgical table (20). As further shown in FIGS. 1 to 3, conventional draping systems, with which the sterile radiological drape (10) of the current invention is designed to operate, include both a conventional patient or table drape (22) that covers the patient (24) and drapes over the edges of the surgical table (20), as well as a cover (26) that encompasses the upper imaging unit (14).

As becomes clear from an examination of the above illustrations, the sterile radiological drape (10) of the current invention is designed for use in conjunction with a standard surgical table (20) and a conventional surgical drape (22) to extend the sterile zone of the surgical environment in a controlled manner to include any radiological equipment (12) that may be needed. Specifically, as shown in FIG. 1 any surgical environment can be divided into two zones, a sterile and an unsterile area, that are generally defined by the plane formed by the top of the surgical table (20). The sterile area extends to all equipment positioned on or above the surface of the surgical table. The radiological sterile drape (10) of the current invention is designed to be either integrated with or attached to the conventional surgical drape (22) at a position on the surgical table (20) within this sterile area. Positioned as shown in FIGS. 2 to 4, it is possible to use the sterile radiological drape (10) to create a sterile envelope or pouch (28) into which the radiological equipment (12) may be inserted and moved. Moreover, as illustrated in FIGS. 3 and 4 the elongated design of the sterile radiological (10) drape of the current invention, which as shown runs substantially the length of the longitudinal axis of the surgical table (20), allows for the free movement of the radiological unit (12) both laterally along the longitudinal axis of the surgical table, as well as vertically either above or below the horizontal plane of the surgical table.

Figure 5:
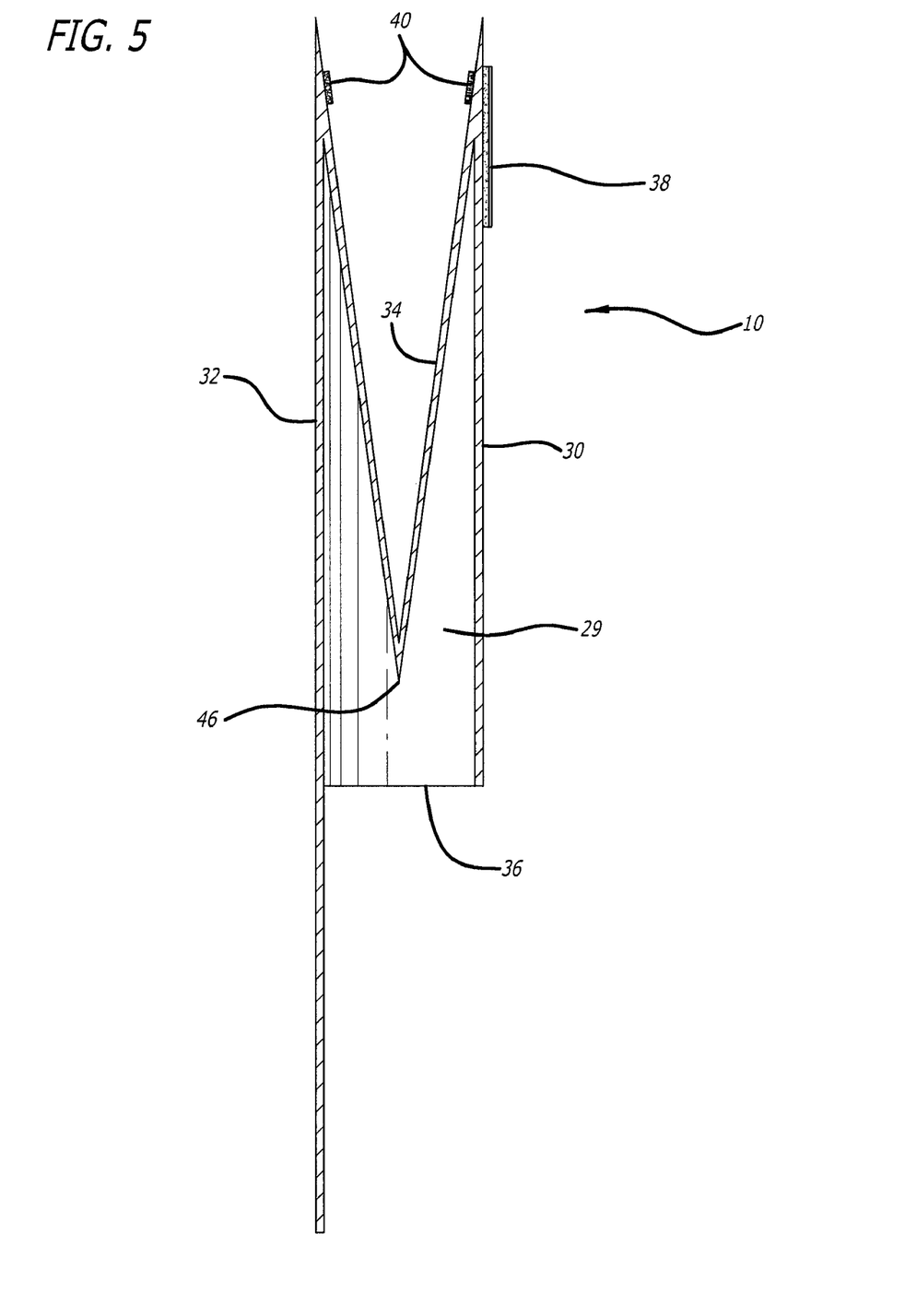
FIG. 5 provides a side cross-sectional view of an embodiment of a sterile radiological drape in accordance with the current invention.
Figure 6:
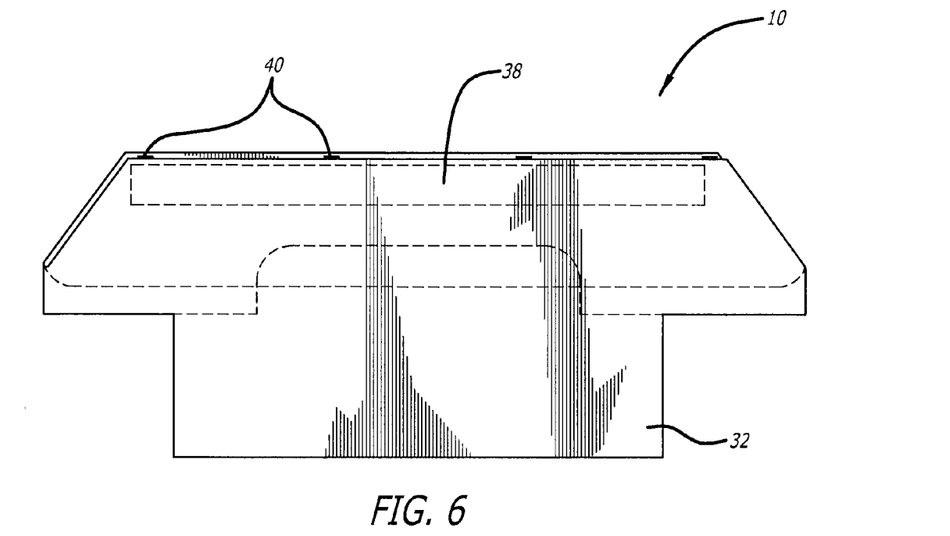
FIG. 6 provides a front elevation view of an embodiment of a sterile radiological drape in accordance with the current invention.
Figure 7:
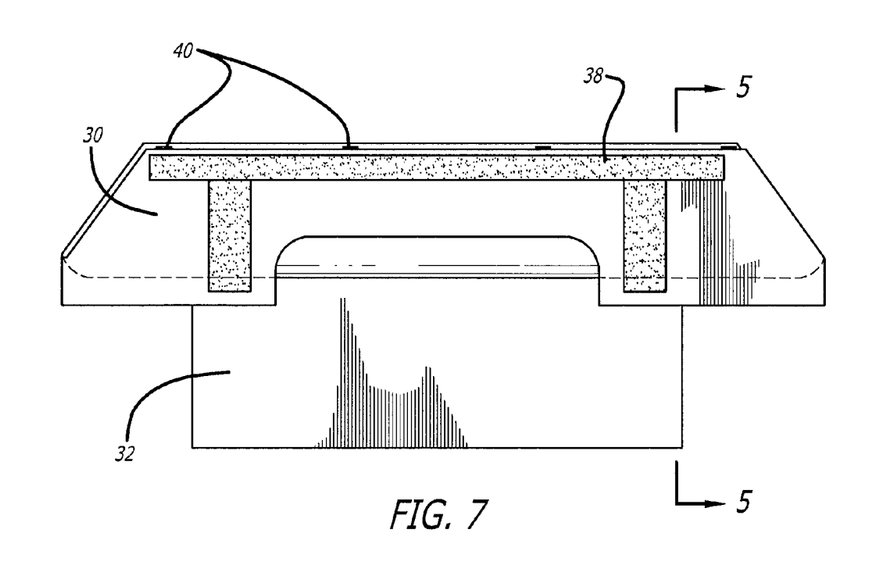
FIG. 7 provides a rear elevation view of an embodiment of a sterile radiological drape in accordance with the current invention.

The construction of the sterile radiological drape (10) of the current invention may be better understood with reference to FIGS. 5 to 7. In broad terms, as shown best in the cross-sectional view provided by FIG. 5, the sterile radiological drape (10) of the current invention comprises an asymmetric pouch or envelope (29) comprising a first side (30) designed to be positioned proximal to the surgical table (20) and a second side (32) designed to be positioned distal to the surgical table, the two sides being interconnected on three edges via a collapsible interconnecting pouch (34). As further shown in FIG. 5, the asymmetry of the sterile radiological drape (10) is created by the difference in vertical lengths of the first (30) and second (32) sides. Specifically, the first proximal side (30) of the sterile radiological drape (10) is designed with a vertical length short enough to ensure that the lower unit (16) and interconnecting C-arm (18) may be inserted beneath the surgical table (20) without being impeded by the sterile radiological drape (10) of the current invention. In contrast, the second distal side (32) of the sterile radiological drape (10) is designed to have a vertical length sufficient to ensure that the lower unit (16) and interconnecting C-arm (18) are fully covered when extended to their maximum vertical position relative to the horizontal plane of the surgical table (20). Although in the figures the second distal side (32) of the sterile radiological drape (10) is shown having a "T" shaped profile, it should be understood that any shape may be used that is suitable to provide sufficient coverage to the radiological unit (12). Finally, although the sidewalls (36) of the interconnecting pouch (34) are shown as interconnecting the opposing faces of the first proximal (30) and second distal (32) sides in a straight-line from the bottom of the first proximal side (30), it should be understood that the sidewalls may interconnect the sides of the sterile radiological drape (10) in any manner that provides coverage to the radiological unit (12) in any position during its operation.

The first proximal side (30) is also provided with one fastener, also referred to as at least one attachment means for attaching the sterile radiological drape (10) of the current invention to the surgical table (20) via the conventional drape (22). As shown in FIGS. 5 to 7, in a preferred embodiment this attachment means comprises a plurality of adhesive strips (38) designed to securely affix the sterile radiological drape (10) to the surgical table (20). Although the above description only discusses adhesive attachment means, it should be understood that any suitable means for attaching the drape to the surgical table may be used, such as, for example, Velcro, snaps, latches, hooks, clamps, clips, zippers, etc. In addition, although the embodiment shown in the figure is a separate unit designed to be attached to the conventional drape (22), it should be understood that the radiological drape (10) may also be integrated with the conventional drape. In such an embodiment the proximal side (30) of the radiological drape (10) would merge with the conventional drape (22) and the attachment means (38) would be unnecessary.

Turning to the construction of the collapsible interconnecting pouch (34), as shown in FIG. 5 the pouch is designed to expand and collapse repeatedly. To accomplish this objective the internal opposing faces of the first proximal (30) and second distal (32) sides of the drape are provided with cooperative interconnecting means (40) that allow the pouch to be secured in a collapsed position when not in use, as shown in FIGS. 5 to 7. Although a specific number and arrangement of these interconnecting means are shown in the figures, it should be understood that any number and arrangement of interconnecting fastener, also referred to as interconnecting means (40) suitable for securing the drape (10) in a collapsed position may be used. It should be further understood that any interconnecting means suitable for allowing the repeated connection and disconnection of the first proximal and second distal sides of the drape when expanded and collapsed may be used, such as, for example, hook and latch connectors, reusable adhesives, snaps, latches, hooks, clamps, clips, zippers, etc.

Figure 8:
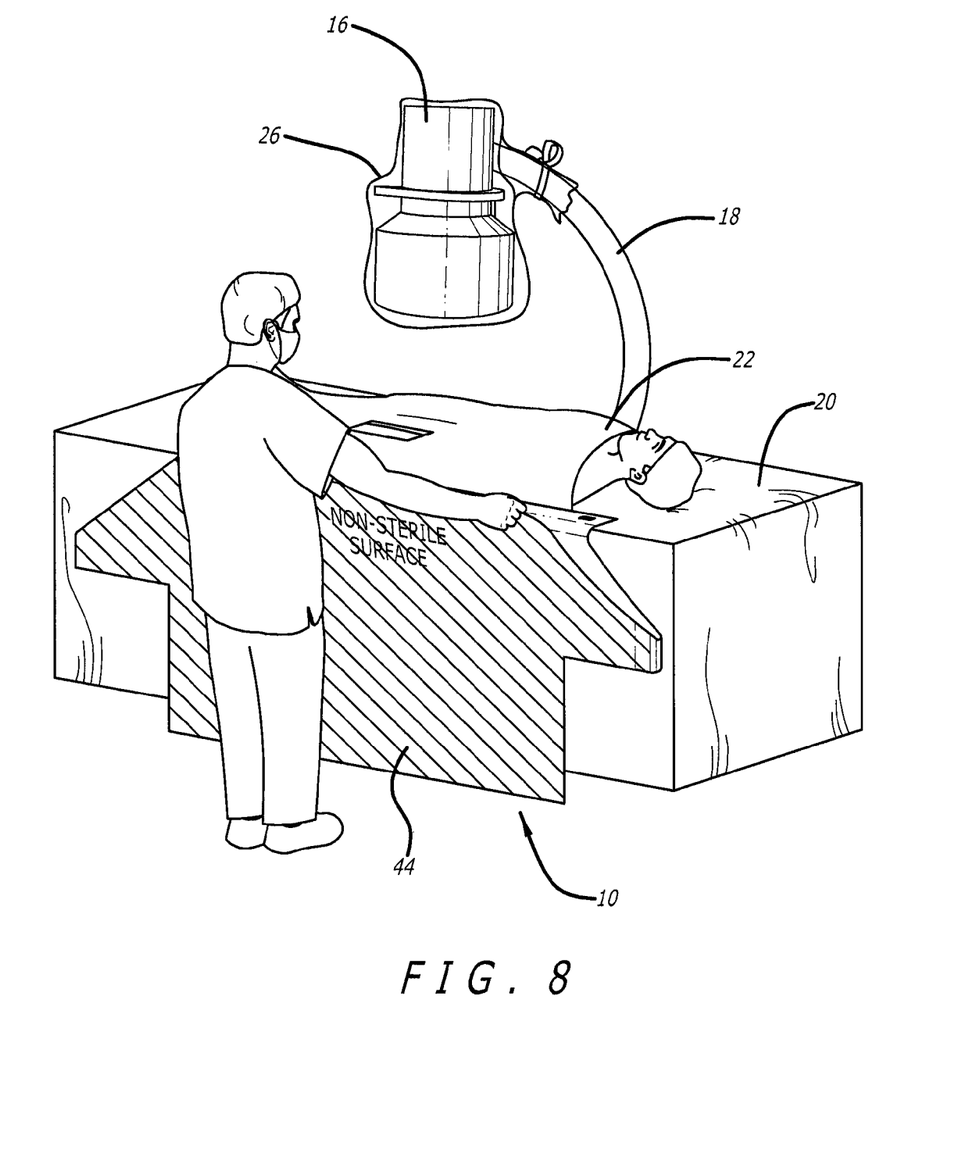
FIGS. 8 and 9 provide perspective views of an embodiment of the sterile and non-sterile zones of a sterile radiological drape in accordance with the current invention.
Figure 9:
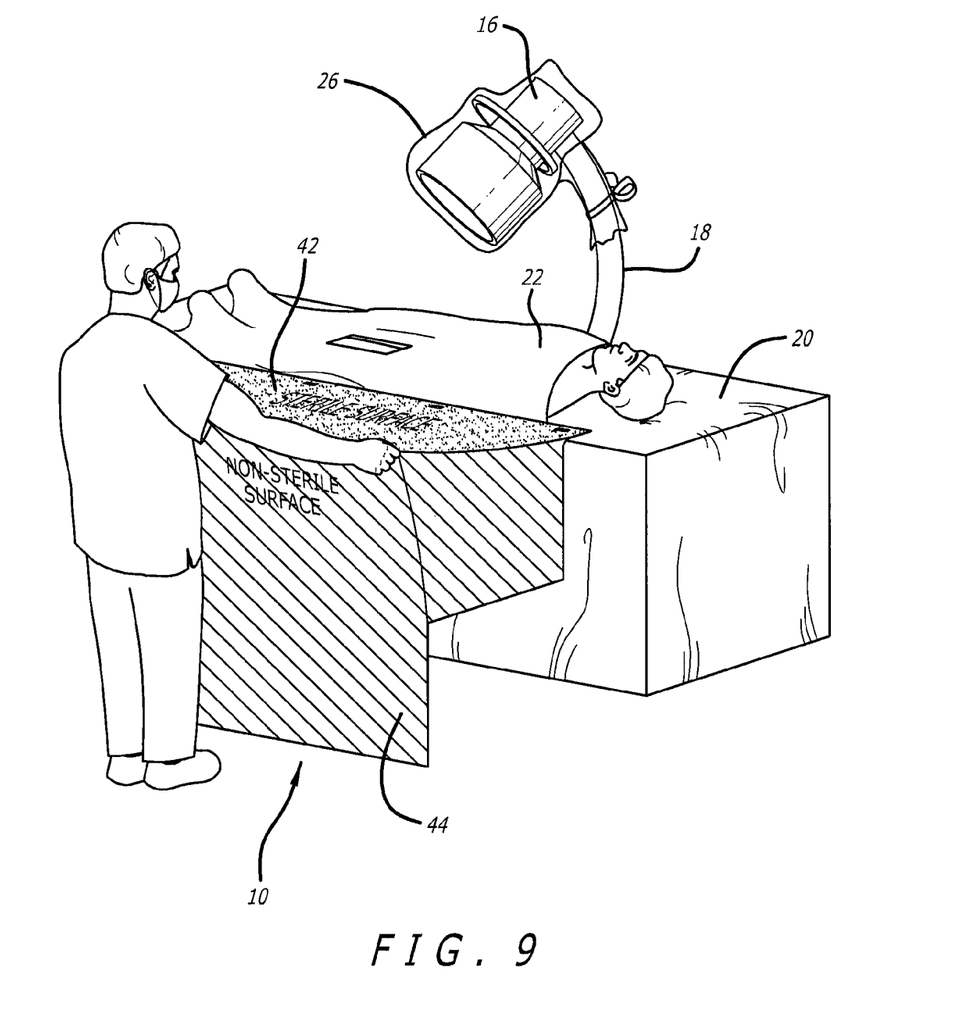

As previously discussed, the fundamental purpose of the sterile radiological drape (10) of the current invention is to provide a secure extension of the sterile zone defined by the horizontal plane of the surgical table (20). As shown in FIGS. 8 and 9, the portion of the sterile radiological drape (10) of the current invention that provides this extended sterile zone is principally formed by the upper outer surfaces (42) of the collapsible interconnecting pouch (34), while the lower surfaces of the sterile radiological drape (10), such as the outer surfaces of the second distal side (44) are substantially non-sterile. Accordingly, to maintain the sterility of the sterile zone (42) of the sterile radiological drape (10), it is important to ensure that the relevant surfaces of the collapsible interconnecting pouch (34) do not touch any of the non-sterile surfaces of the drape (10). To this end, as best shown in FIG. 5, the collapsible interconnecting pouch (34) is designed with at least one pleat (46) in the sidewalls (36) of the pouch such that the pouch (34) folds in upon itself when collapsed. Although only a single pleat (46) is shown in the exemplary embodiment of FIG. 5, it should be understood that any number or arrangement of pleats or other folding means suitable for ensuring that the sterile surfaces (42) of the collapsible interconnecting pouch (34) remain inwardly arranged such that they do not come into contact with any of the non-sterile zones of the drape (10) or the wider surgical theater may be used. As an added advantage, because the collapsible interconnecting pouch (34) remains sterile both when expanded and when collapsed, the pouch can also be utilized as a sterile place for the temporary placement and storage of instruments in use during the surgical procedure, such as, for example, suction tubing, bovie cautery, etc.

Turning now to the construction of the sterile radiological drape (10) of the current invention, it should be understood that any material suitable for use in the sterile environment of an operating theater may be used. In a preferred embodiment the drape is made of a plastic material; however, other suitable materials may be used, such as, for example, cloth, paper, synthetics or a composite of several materials.

Although the above discussion illustrates each of the essential features of the sterile radiological drape of the current invention, it should be understood that other optional features may be included to enhance the functionality of the drape. The following provides a description of some exemplary optional features; however, it should be understood that these improvements are only included for illustration and one skilled in the art may conceive of numerous other possible modifications that would not change the structure and function of the basic device.

In one exemplary embodiment, the sterile radiological drape may optionally include a reinforcement liner surrounding the edges of the drape to ensure the integrity of the sterile zone.

In another exemplary embodiment, either the entire radiological drape, or at least the portion of the sterile radiological drape into which the lower unit of the radiological unit is positioned, can made of a transparent material such that the operator of the unit can more easily visualize and position the unit to allow for the successful imaging of the patient.

In still another exemplary embodiment, the entire radiological drape, or at least those portions of the drape which are in the sterile zone may be coated, imbued with or made from an appropriate antibacterial, antifungal and/or antiviral material.

In yet another exemplary embodiment, the sterile and non-sterile portions of the radiological drape may be color coded to provide the surgical team with a visual gauge as to the division between these zones as the radiological unit is moved into, through and out of the surgical theater.

In still yet another exemplary embodiment, the lower edges of the radiological drape may be weighted to ensure that the drape is not inadvertently raised either by a member of the surgical team or by the movements of the radiological unit.

In still yet another exemplary embodiment, the sterile radiological drape may be provided with additional fasteners, elasticized gathers, or pleats to ensure that the drape conforms to and engages more securely with the radiological unit when in the desired imaging position.

Figure 10:
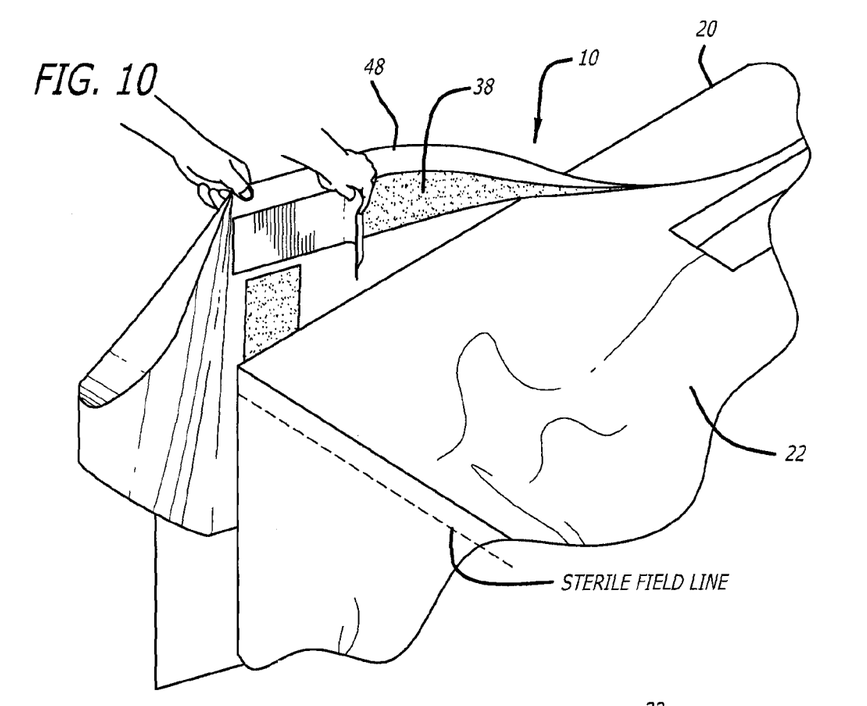
FIG. 10 provides a perspective view of the operation of an embodiment of a sterile radiological drape in accordance with the current invention.

Although the above discussion has focused exclusively on the design and features of the device itself, the current invention is also directed to a method of draping a patient during a surgical procedure requiring imaging that uses the unique features of the inventive drape. The operation of the sterile radiological drape of the current invention will be better understood with reference to FIGS. 10 and 11. As shown in FIG. 10, in a first step the sterile radiological drape (10) must be attached to the surgical table (20). To accomplish this first the upper longitudinal edge (48) of the drape (10) is positioned on top of the conventional table drape (22) within the sterile zone defined by the horizontal plane of the surgical table (20).

Once in position, the drape is secured to the surgical table (20) through the conventional table drape (22) via the attachment means (38). In the embodiment shown in FIG. 10 and discussed above, the attachment means are a series of adhesive strips. Accordingly, in this embodiment the protective covers of the adhesive strips (38) are removed and the adhesive strips attached to the conventional table drape (22) as described above. As indicated above, although three adhesive strips providing attachment both horizontally and vertically are shown in the embodiment illustrated in FIG. 10, it should be understood that any number and arrangement of attachment means may be provided such that a suitably secure attachment between the sterile radiological drape (10) and the conventional table drape (22) is formed. Alternatively, if the sterile radiological drape (10) is integrated into the conventional table drape (22), then this initial step this initial step only requires positioning the combined conventional and radiological drape appropriately over the patient.

Figure 11:
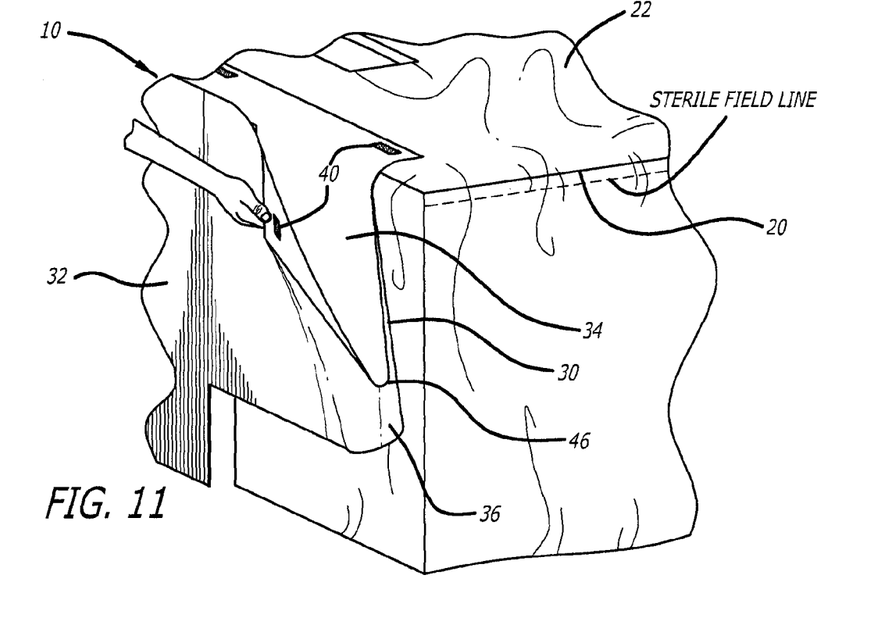
FIG. 11 provides a perspective view of the operation of an embodiment of a sterile radiological drape in operation in accordance with the current invention.

Once in position, the pleated (46) plastic at the base and sides (36) of the drape (10) allows the drape to lie flat against the conventional sterile table drapes (22) above the edge of the sterile field boundary so as not to interfere with the operative procedure. As shown in FIG. 11, the collapsed sides of the drape will adhere together to ensure that the drape lies flat via the pre-placed interconnecting means (40), such as, for example, hook and latch connectors like Velcro tabs. As further shown in FIG. 11, when required by the insertion of the radiological equipment, the interconnecting means (40) are separated and the drape expanded to accept the un-sterile working portion of the radiological unit (14) as the machine is rotated into a lateral (horizontal) position. Excess material on the second distal side (32) of the drape (10) will cover the portion of the radiological unit (12) furthest from the sterile field, as shown in FIGS. 2 to 4. The portion of the drape (42) entering the sterile field is sterile when expanded, as shown best in FIGS. 8 and 9, and remains sterile even when the radiological unit is removed as the sterile surface (34) folds in upon itself when collapsed. When the radiological unit (12) is removed and the drape (10) collapsed, the interconnecting means (40) are reengaged one to the other to ensure the integrity of the sterile surfaces (34) of the drape, and to fold the drape (10) flat against the table (20) such that it does not interfere with the operative procedure when not in use. In this manner the radiological unit can be moved into and out of the surgical environment, and the drape (10) expanded and collapsed, as often as necessary during the operation.

In summary, the sterile drape of the current invention isolates the radiological unit thereby improving the security of the sterile field, and as a result reducing the risk of nosocomial infection. The surgical drape will also reduce surgical time and eliminate the risk, expense, and hassle of utilizing multiple half sheets. In addition, because of the unique construction of the sterile drape of the current invention it is possible to repeatedly expand and collapse the drape without compromising the sterile portion of the drape. As a further advantage the pleated or folded portion of the drape may also be used as a sterile instrument holding pouch. Finally, by modifying the drape additional advantages can be engineered into the drape of the current invention, such as, for example, a transparent window to provide for the direct visualization of the central beam emitter, color coded regions for indicating to the operating staff the sterile and non-sterile portions of the drape, the incorporation of antibacterial materials into the drape itself, and additional reinforcement, fasteners and pleats to improve the fit and function of the drape in conjunction with the radiological equipment, among others.

While the above description contains many specific embodiments of the invention, these should not be construed as limitations on the scope of the invention, but rather as an example of one embodiment thereof. For example, although specific fasteners, dimensions and configurations for the drape are provided, as discussed throughout this disclosure other schemes may be used. Moreover, the principle of this radiological drape is not limited to the specific construction described herein, but can be extended to use other constructions that allow for the drape to be repeatedly engaged and disengaged without compromising the sterile portion of the drape. Accordingly, the scope of the invention should be determined not by the embodiments illustrated, but by the appended claims and their equivalents.

What is claimed is:

1. A sterile imaging drape for use on an operating table in conjunction with mobile imaging equipment to preserve the sterile field of the operating theater comprising:

a flexible enclosure comprising a proximal portion, a distal portion and a pouch disposed therebetween and interconnecting said proximal and distal portions, the pouch including at least an inner imaging equipment contacting surface and an outer upper sterile portion and having two side portions disposed between said proximal and distal portions on laterally opposing sides of the upper sterile portion wherein the pouch can repeatedly take one of either an expanded or a collapsed configuration, where in the expanded configuration the pouch is sufficiently dimensioned such that the enclosure may receive and cover at least a portion of the mobile imaging equipment, and where in the collapsed configuration the outer upper sterile portion of the expandable pouch is folded inwardly such that the outer upper sterile portion is substantially shielded from external contamination;

at least one anchor fastener disposed on the proximal portion to fixedly attach the enclosure to a portion of the operating table within the sterile field; and at least one reusable enclosure fastener disposed adjacent at least one of said proximal and distal portions to secure the enclosure in the collapsed configuration.

2. The sterile imaging drape of claim 1, wherein the enclosure is asymmetric.

3. The sterile imaging drape of claim 2, wherein the proximal portion has a smaller vertical dimension relative to the distal portion such that an opening is provided through which the mobile imaging equipment may be inserted into the enclosure.

4. The sterile imaging drape of claim 2, wherein the distal portion has a longer vertical dimension relative to the proximal portion such that distal portion fully covers the mobile imaging equipment regardless of the vertical alignment of the mobile imaging equipment relative to the operating table.

5. The sterile imaging drape of claim 4, wherein the distal portion takes the form of a "T" shaped sheet.

6. The sterile imaging drape of claim 1, wherein said side portions have vertical dimensions that match the vertical dimension of the distal portion.

7. The sterile imaging drape of claim 1, wherein said side portions have vertical dimensions that match the vertical dimension of the proximal portion.

8. The sterile imaging drape of claim 1, wherein said side portions have a vertical dimension that varies along its length such that the ends of the side portions adjacent the proximal portion match the vertical dimension of the proximal portion, and the ends of the side portions adjacent the distal portion match the vertical dimension of the distal portion.

9. The sterile imaging drape of claim 1, wherein the proximal and distal portions are each interconnected to the pouch on three edges.

10. The sterile imaging drape of claim 1, wherein the enclosure includes a plurality of anchor fasteners.

11. The sterile imaging drape of claim 1, wherein the at least one anchor fastener is selected from the group consisting of adhesives, hooks and loops, snaps, latches, hooks, clamps, clips and zippers.

12. The sterile imaging drape of claim 1, wherein the at least one reusable enclosure fastener comprises cooperative interconnection means disposed on opposing faces of the proximal and distal portion.

13. The sterile imaging drape of claim 1, wherein the at least one reusable enclosure fastener is selected from the group consisting of adhesives, hook and latch connectors, snaps, latches, hooks, clamps, clips and zippers.

14. The sterile imaging drape of claim 1, wherein the pouch is formed with at least one pleat.

15. The sterile imaging drape of claim 1, wherein the enclosure is formed of a material selected from the group of plastic, cloth, paper, synthetics and composites thereof.

16. The sterile imaging drape of claim 1, further comprising a reinforcement liner disposed along the edges of the enclosure.

17. The sterile imaging drape of claim 1, wherein the at least a portion of the enclosure is transparent.

18. The sterile imaging drape of claim 1, wherein at least a portion of the enclosure includes an active material selected from the group of antibacterial agents, antifungal agents and antiviral agents.

19. The sterile imaging drape of claim 18, wherein the active material is included in the enclosure by a technique selected from the group of coating, imbuing, and impregnating.

20. The sterile imaging drape of claim 1, wherein the sterile portion of the enclosure is marked with a unique visual indicator.

21. The sterile imaging drape of claim 1, further including at least one weighted element incorporated into at least one of the lower edges of the enclosure.

22. The sterile imaging drape of claim 1, further including at least one additional tailoring means for conforming the shape of the enclosure to the mobile imaging equipment, where the tailoring means is selected from the group of fasteners, elasticized gathers and pleats.

23. The sterile imaging drape of claim 1, wherein the mobile imaging equipment is a fluoroscopy unit and the enclosure is designed to cover the lower C-arm of the fluoroscopy unit.

24. The sterile imaging drape of claim 1, wherein the sterile field is the area above the upper surface of the surgical table.

25. The sterile imaging drape of claim 1, wherein the proximal portion of the enclosure is dimensioned to cover the length of the operating table.

26. A method of draping a patient comprising:
draping a patient with a conventional surgical drape;
providing a sterile imaging drape as set forth in claim 1;
securedly affixing the proximal portion of the sterile imaging drape to the conventional surgical drape; and
expanding the sterile imaging drape from the collapsed configuration to the expanded configuration to accept the mobile imaging equipment and simultaneously exposing the outer upper sterile portion within a sterile field of the surgical theater above a top surface of a surgical table from its substantially shielded configuration.

27. The method of claim 26, further comprising engaging the reusable enclosure fastener to secure the enclosure in the collapsed configuration to fold the outer upper sterile portion of the pouch inwardly such that the outer upper sterile portion is substantially shielded from external contamination while in an unsterile field of the surgical theater below the top surface of the surgical table.

28. The method of claim 26, wherein the step of affixing the drape includes activating the adhesive strip on the proximal portion of the enclosure.

29. A sterile imaging drape for use on an operating table in conjunction with mobile imaging equipment to preserve the sterile field of the operating theater comprising:
a flexible enclosure sized to receive and cover at least a portion of the mobile imaging equipment, said enclosure comprised of a collapsible pouch disposed between proximal and distal ends, said collapsible pouch including an upper sterile surface and a plurality of unsterile side surfaces disposed between said proximal and distal portions on laterally opposing sides of the upper sterile surface, wherein when the distal end is moved distally the pouch expands to allow receipt of the mobile imaging equipment and wherein when the distal end is moved proximally toward the proximal end the pouch collapses and the upper sterile surface of the pouch folds inwardly such that the upper sterile surface is shielded from contamination;

at least one pouch fastener for cooperatively interconnecting the proximal and distal ends of the enclosure when the enclosure is in the collapsed position; and an anchor fastener disposed on the proximal end of the enclosure, said anchor being designed to fixedly attach the proximal end of the enclosure to the operating table within the sterile field.

30. A sterile drape for use on an operating table in conjunction with mobile imaging equipment to preserve the sterile field of the operating theater comprising:

a flexible enclosure comprising a patient portion for covering at least part of the patient and an imaging portion, the imaging portion including a proximal portion, a distal portion and a pouch disposed therebetween and interconnecting said proximal and distal portions, the pouch including at least an upper sterile portion and two side portions disposed between said proximal and distal portions on laterally opposing sides of the upper sterile portion, wherein the pouch can repeatedly take one of either an expanded or a collapsed configuration, where in the expanded position the pouch is sufficiently dimensioned such that the enclosure may receive and cover at least a portion of the mobile imaging equipment, and where in the collapsed position the upper sterile portion of the expandable pouch is folded inwardly such that the upper sterile portion is substantially shielded from external contamination;

at least one reusable enclosure fastener disposed to secure the enclosure in the collapsed configuration.

* * * * *